(12) United States Patent
Sieben et al.

(10) Patent No.: US 6,288,440 B1
(45) Date of Patent: Sep. 11, 2001

(54) CHIP ARRANGEMENT

(75) Inventors: Ulrich Sieben, Reute; Günter Igel, Teningen; Mirko Lehmann, Freiburg; Hans-Jürgen Gahle, Emmendingen; Bernhard Wolf, Stegen; Werner Baumann, Freiburg i.Br.; Ralf Ehret, Merdingen, all of (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 09/342,697

(22) Filed: Jun. 29, 1999

(30) Foreign Application Priority Data

Jun. 30, 1998 (DE) .............................................. 198 29 121

(51) Int. Cl.$^7$ ................................................... H01L 23/495
(52) U.S. Cl. ........................ 257/668; 257/730; 257/777; 361/784; 361/803; 361/807
(58) Field of Search ................................. 257/701–703, 257/668, 730, 777; 174/260; 361/760, 783, 782, 784, 803, 807, 808, 820

(56) References Cited

U.S. PATENT DOCUMENTS

| 3,601,699 | * | 8/1971 | Norton et al. ........................ 324/537 |
| 5,114,859 | | 5/1992 | Kagenow ................................ 436/50 |

FOREIGN PATENT DOCUMENTS

| 28 22 391 A1 | 12/1978 | (DE) . |
| 0 190 005 A2 | 8/1986 | (EP) . |
| 0 399 227 A1 | 11/1990 | (EP) . |
| 07103934 A | 4/1995 | (JP) . |
| WO 87/05747 | 9/1987 | (WO) . |
| WO 97/42478 | 11/1997 | (WO) . |

* cited by examiner

Primary Examiner—Timothy P. Callahan
Assistant Examiner—Minh Nguyen
(74) Attorney, Agent, or Firm—Akin, Gump, Strauss, Hauer & Feld, L.L.P.

(57) ABSTRACT

A chip arrangement (1) has a substrate board (2) with an opening (3), into which a carrier chip (4) is inserted, which has an electrical or electronic structural component (5). At least one conductor path (7) is integrated into the carrier chip (4), which connects the structural component (5) to the electrical connection contact (8). The carrier chip (4) is inserted into the opening (3) in such a way that its ends project beyond the opposite-facing, flat-sided surfaces (9, 9') of the substrate board (2), and thereby form overhangs (10, 10'). Here, the structural component is arranged on the overhang (10) projecting beyond the one surface (9), and the connection contact (8) is arranged on the overhang (10') projecting beyond the other surface (9'), and the conductor path (7) connecting the structural component (5) and the connection contact (8) passes through the opening (3). A seal is arranged between the substrate board (2) and the carrier chip (4).

23 Claims, 4 Drawing Sheets

CHIP ARRANGEMENT

BACKGROUND OF THE INVENTION

The invention involves a chip arrangement having a substrate plate or board, which has at least one passage through it, into which a carrier chip is inserted. A carrier chip surface has at least one integrated conductor path that connects at least one electrical or electronic structural component, in particular a sensor, with at least one electrical connection contact.

A chip arrangement of this type has become known through obvious prior use on the market. It is used to examine biological cells, which are settled in a nutrient medium on the surface of the substrate plate and the support chip inserted therein. In the support chip of the previously known chip arrangement, a sensor is integrated, with which measurement signals are detected at the cells or the nutrient medium and can be guided further via conductor paths to a measurement device and evaluation device. So that the chip arrangement can be handled well in practice, it has proven expedient if it has a certain minimum size and is constructed, for example, as an essentially rectangular board with a size of 2.5×3 cm. Since semiconductor chips of this size are relatively expensive to manufacture, in the previously known chip arrangement, a carrier chip having the sensor is inserted into a substrate board made of glass. The chip arrangement can thereby be handled well, and nevertheless the dimensions of the carrier chip can be selected to be relatively small, so that the chip arrangement can be manufactured in a correspondingly cost-effective manner.

In the previously known chip arrangement, the carrier chip is inserted into the opening located in the substrate board in such a way that the surface of the carrier chip, which has the conductor paths, essentially connects in a flush manner onto a flat-sided surface of the substrate board, which also has conductor paths. For this purpose, the conductor paths of the carrier chips are connected via bonding compounds to those of the substrate board. The conductor paths of the substrate board lead to connection contacts which are connectable to a measurement and evaluation device. In the area of the bonding compounds of the conductor paths, bonding pads are arranged respectively on the carrier chip and on the substrate board.

So that the conductor paths of the carrier chip are electrically insulated from a medium to be examined, for example a nutrient medium with biological cells, they are covered with a passivation layer, which is applied in the manufacture of the carrier chip using masking technology. Since the bonding pads must be accessible when applying the bonding compounds that connect the carrier chip with the substrate board, the passivation layer has a recess in the respective area of the bonding pad. The bonding pads are therefore poured, after application of the bonding compounds, into an electrically insulating plastic mass, which encloses the bonding pads and the bonding compounds applied on them. This sealing of the bonding pads with plastic has, however, proven to be of little reliability in practice, since the nutrient medium for the cells to be examined, which is located in the area of the sensor in the use position of the chip arrangement, contains ions and salts which can infiltrate the plastic mass. A gap thereby forms between the plastic mass and the substrate board, through which the ions or salts can reach the bonding pads. Here, the danger exists on the one hand, that leak currents, which falsify the measurement signals, form between the bonding pads and the nutrient medium, and on the other hand, the salts and ions contained in the nutrient medium also cause, however, corrosion on the bonding pads, which reduces the lifetime of the chip arrangement.

From Japanese published patent application (kokai) JP 07103934 A, a chip arrangement is also already known, in which the carrier chip lies flat, with its rear side facing away from the electrical structural component, on the flat-sided surface of a substrate board and is connected to it. Here, the electrical connection between the carrier chip and the substrate board is made using a through-contact penetrating the substrate board, which leads from the rear side of the carrier chip to the rear flat side of the substrate board that faces away from the carrier chip. The connection lines to a measurement and evaluation device can thus be connected to the rear side of the substrate board that is facing away from the medium to be examined, whereby corrosion formation on the bonding pads and/or conductor paths is prevented. It is unfavorable, however, in this process, that the through-contact can only be realized with a relatively large production engineering expense, which is why the manufacture of the chip arrangement is comparatively time-intensive and expensive.

SUMMARY OF THE INVENTION

An object of the invention is therefore to create a chip arrangement of the type described at the outset, which has a good corrosion-resistance with respect to a medium to be examined or treated with the electrical or electronic structural component, and which nevertheless can be manufactured in a simple and cost-effective manner.

The solution of this object consists in that the carrier chip is inserted into the through opening in such a manner that it extends with its ends beyond the flat-sided surfaces of the substrate board which face away from each other, and thereby forms overhangs; that on the overhang that extends beyond the one surface, the structural component is arranged and on the overhang extending beyond the other surface, the connection contact is arranged; that the conductor path connecting the structural component and the connection contact to each other goes through the opening of the substrate board; and that between the substrate board and the carrier chip, a seal is provided.

The carrier chip is thus arranged with its chip plane transverse to the extension plane of the substrate board and penetrates it, so that on the two surfaces of the substrate board that face away from each other, a respective portion of the carrier chip projects beyond the respective surface of the substrate board and forms an overhang there. Here, the electrical or electronic structural component is arranged on the overhang that is located on the one substrate board surface, and the connection contact connected via the conductor path integrated in the carrier chip is arranged on the overhang located on the other substrate board surface. The connection contact is thus located on the rear side of the substrate board, which faces away from the electrical or electronic structural component, so that the conductor path areas located in the area of the overhang having the structural component can be completely covered by a passivation layer. Such a passivation layer can, for example, be manufactured by thin-film technology with great accuracy and resistance to moisture, so that corrosion on the conductor path integrated in the carrier chip by the medium that is to be examined or treated with the electrical or electronic structural component is prevented to the greatest extent possible.

The seal arranged between the carrier chip and the substrate board prevents the medium located on the front side of the substrate board from reaching the connection contact arranged on the rear side of the substrate board. The opening arranged in the substrate board can, for example, be made in the substrate board using ultrasonic drilling. The chip arrangement can thus be manufactured in a simple and cost-effective manner. Since a plastic mass for pouring-in of bonding pads can be omitted, the chip arrangement has, moreover, especially compact dimensions.

Expediently, the carrier chip can be detachably connected to the substrate board. The carrier chip can then, if necessary, be easily replaced, when the structural component has reached its planned lifetime or if it should ever break down through contact with a chemically aggressive medium that is to be examined or treated.

In a preferred and especially advantageous embodiment of the invention, the carrier chip is adhered to a wall area of the substrate board which borders the opening. The adhesive arranged between the carrier chip and the substrate board then functions, on the one hand, for the purpose of affixing the carrier chip to the substrate board and, on the other hand, however, also seals off the opening of the substrate board from the carrier chip, so that a medium located on the front side of the substrate board in the area of the electrical or electronic structural component can not reach the rear side of the substrate board that has the connection contact. The adhesive, moreover, offsets tolerances in the dimensions of the carrier chip and/or the wall opening located in the substrate board, into which the carrier chip is inserted. The chip arrangement can in this way be manufactured in an even simpler and more cost-effective manner.

Expediently, the carrier chip is arranged with its extension plane at a right angle to a flat-sided surface of the substrate board. The side surfaces of the substrate board bordering the opening can then be arranged at a right angle to its flat-sided surface, which makes it easier to form the opening in the substrate board.

An especially advantageous embodiment of the invention provides that the carrier chip surface that has the electrical or electronic structural component is arranged at an incline to the flat-sided surface of the substrate board and preferably encloses an acute angle with it. The electrical or electronic structural component is then arranged in a corner area that is bordered by the carrier chip and the substrate board, so that only particles which do not exceed a size prescribed by the dimensions of the corner area, can come into contact with the electrical or electronic structural component. Thus, a mechanical filter that is constructed in a simple manner results, which prevents larger particles from pushing forward to the structural component.

A preferred embodiment of the invention provides a tapering of the cross-section of the overhang, which has the electrical or electronic structural component and proceeds from the surface of the substrate board to the position of the overhang that projects out the furthest. The overhang having the structural component thus has a point. In a chip arrangement in which the electronic structural component is a sensor, the substrate board can, for example, be placed with its flat side on a skin layer to be examined, wherein the pointed overhang having the sensor penetrates into the skin layer, by a defined depth corresponding to the height of the overhang, so that measurement values can be gathered there. Thus, for example, the glucose concentration, the moisture of the skin, an ion concentration, a gas content or similar physiological parameters can be measured, which make possible statements about the vitality of the skin and/or the tissue area located behind it. For this purpose, it is even possible that the substrate board lying on the skin layer is moved parallel to the surface of the skin layer, so that the overhang having the sensor is pulled through the skin parallel to the surface of the skin layer. In a simple manner, a measurement profile can thereby be made along a line running parallel to the surface of the skin layer. Of course, the chip arrangement having the pointed overhang can also, however, be used to examine or treat other soft bodies, into which the pointed projection having the electrical or electronic structural component can penetrate while pressing the substrate board onto the body.

An advantageous embodiment of the invention provides that the carrier chip can be inserted at at least two different positions into the opening of the substrate board during the assembly of the chip arrangement. In one of these positions at least one electrical or electronic structural component is arranged on an overhang of the carrier chip projecting beyond a flat-sided surface of the substrate board, and the connection contact(s) allocated to this(these) structural component(s) are arranged on the overhang extending beyond the other flat-sided surface of the substrate board. In the other position of the carrier chip, the structural component(s) and the connection contact(s) are arranged on the same overhang of the carrier chip which extends beyond a flat-sided surface of the substrate board. In this manner, it is possible by suitable insertion of the carrier chip into the substrate board, only for the duration of a measurement or a treatment, to bring the structural component into contact with an object located on a flat-sided surface of the substrate board, for example a chemically aggressive medium, while the structural component is arranged outside of the measurement phase or treatment phase on the flat-sided surface of the substrate board facing away from the object. The structural component thus comes only temporarily into contact with the aggressive medium, such that its lifetime is correspondingly prolonged.

In an especially advantageous further embodiment of the invention, it is provided that the carrier chip is insertable during the assembly of the chip arrangement into at least two different positions in the opening of the substrate board. The carrier chip has at least two electrical or electronic structural components, which are respectively connected by at least one conductor path to at least one electrical connection contact respectively allocated to them. Depending on the selected position of the carrier chip, at least one of these structural components is arranged respectively on an overhang of the carrier chip extending beyond a flat-sided surface of the substrate board, and the connection contact allocated to this(these) structural component(s) is arranged on the overhang extending beyond the other flat-sided surface of the substrate board. In this manner, depending on the selected position of the carrier chip, another structural component or even several other structural components are arranged on the overhang of the carrier chip facing towards the object to be examined or treated in the usage position. In a carrier chip having several equivalent structural components, the lifetime of the chip arrangement becomes prolonged accordingly by this, since a structural component, which for example has become unusable through a longer contact with a chemically aggressive medium, can be replaced by suitable conversion of the carrier chip in a simple way through another, functional structural component.

The carrier chip can, however, also have structural components that are different from each other. A building kit for creating a chip arrangement thereby results, with which different chip arrangements can be made depending on the selected position of the carrier chip in the opening of the substrate board. The electrical or electronic structural components can, for example, be distributed on the circumference of the carrier chip, integrated in its flat-sided surface, such that the carrier chip can be inserted into the substrate board in different rotational positions relative to the normals on this surface. Depending on the respective rotational position of the carrier chips, respective other structural components or sensors are then arranged on the front side of the substrate board, while the connection contacts allocated to them are located respectively on the rear side of the substrate board.

It is advantageous if, on the electrical or electronic structural component, a membrane is arranged which can be permeated by ions. Ions can thereby reach the structural component or the sensor, while other substances can be kept away from the sensor by the membrane. It is even possible here, that the membrane is only permeable for certain ions, so that their concentrations can be selectively measured in a medium to be examined. Expediently, the membrane is applied on the electrical or electronic structural component after the insertion of the carrier chips into the substrate board. For this purpose, the membrane material is then dissolved in a volatile liquid, for example in alcohol or acetone. The chip arrangement is oriented in a manner such that the surface of the carrier chip having the structural component runs at an angle to the horizontal, in particular vertical. Then, on the front side edge surface of the carrier chip, which is adjacent to the structural component and runs transverse to the surface of the carrier chip having the structural component, a small quantity of the liquid that contains the membrane material is applied, so that a part of this liquid flows by gravity flow from the front side edge surface of the carrier chip over the electrical or electronic structural component located on the surface of the carrier chip arranged transverse to it, so that a thin liquid layer forms on it. After the evaporation of this liquid layer, a membrane layer remains on the electrical or electronic structural component, which has a uniform thickness on the structural component.

In an advantageous embodiment of the invention, in the area of the measurement space or active space of the electrical or electronic structural component, the substrate board has at least one projection, which forms a mechanical filter together with the overhang having the structural component. Here, for a structural component that sends out electromagnetic radiation, active space is understood to be the space into which the structural component sends out the radiation. Correspondingly, for a structural component from which an electrical and/or magnetic field is emitted, the space is understood to be the space in which the field is active. The mechanical filter thus has a projection acting together with the overhang having the structural component, where between the structural component and the projection a free space is arranged, which forms the access to the structural component. Particles having dimensions larger than those of the free space of the measurement space or active space of the structural component are thereby kept away, while smaller particles can reach the measurement or active space and possibly up to the structural component itself. The projection can also be a shoulder or a step located on the substrate board.

One embodiment provides that the projection of the mechanical filter is formed by the overhang of a small board that is inserted into an opening of the substrate board. The projection can then be mounted on the substrate board in the same way during the manufacture of the chip arrangement, as the overhang of the carrier chip having the electrical or electronic structural component. The chip arrangement is thereby manufactured in a much simpler way. Optionally, the projection of the mechanical filter can also be formed by the overhang of an additional carrier chip.

In order to filter small particles, for example those having a diameter which is smaller than 1 $\mu$m, it is advantageous if a body rests on the carrier chip and covers the electrical or electronic structural component. As a spacer on the carrier chip, at least one area adjacent to the body and projecting laterally beyond the surface plane of the structural component, and/or on the body, an area adjacent to the carrier chip and projecting laterally over the surface area covering the structural component is arranged, so that between the structural component and the body an open space or gap forming access to the structural component is arranged. The body can thereby be positioned during the assembly of the chip arrangement in a simpler manner and with greater precision on the carrier chip.

The area projecting opposite the structural component can be manufactured with known processes of semiconductor technology, for example by masking technology, with great dimensional accuracy, which makes possible especially the creation of small gap dimensions or open spaces between the structural component and the body with tight tolerated dimensions. The body adjacent to the projecting carrier chip area can have an essentially flat surface area that faces towards the structural component and is arranged parallel to its surface plane, and preferably is adjacent to the projecting carrier chip area. The body can be, for example, a second carrier chip, which lies flat on the projecting area of the first carrier chip. The manufacture of the carrier chip area projecting opposite the structural component can, for example, occur in such a manner that, in the surface of the carrier chip, a recess is etched, in which the structural component is arranged or that, at certain positions of the surface of the carrier chip, at least one layer is vacuum metallized or applied.

It is advantageous if the carrier chip surface having the electrical or electronic structural component and the facing surface of the projection arranged in the area of the measurement or active space of the structural component run at a slant to each other in the shape of a funnel in the surface plane of the substrate board. In this way, a funnel-shaped channel results which forms a flow direction-dependent filter for a medium located on the substrate board.

For an examination or treatment of biological cells, it is advantageous if the spacing between the electrical or electronic structural component and the projection(s) arranged in the area of its (their) measurement space or active space, is adapted to the diameter of a biological cell and is preferably larger than 4 $\mu$m and smaller than 55 $\mu$m. A cell can thereby settle directly on the structural component between the overhang having the electrical or electronic structural component and the projection, while particles whose dimensions are larger than the cell diameter are kept away from the structural component.

It is especially advantageous if at least two carrier chips are inserted into the substrate board, if one of the carrier chips has at least one structural component constructed as a radiation emitter and the other carrier chip has at least one structural component that is constructed as a receiver and is allocated to the radiation emitter, and if a measurement section is arranged between the radiation emitter and the receiver. With a chip arrangement of this type, for example, a scattered light measurement or transmitted light measurement can be performed. In this way, the two carrier chips can optionally simultaneously also form a mechanical filter, so that only particles up to a certain size, prescribed by the spacing of the carrier chip, can reach the measurement section.

It is advantageous if the substrate board comprises an elastic material, for example an amorphous silicon. The substrate board can then be impinged by a tensile or compression force in the extension direction, in order to change the spacing between the projection of the carrier chip, which has the electrical or electronic structural component, and a projection of the substrate board, which forms a mechanical filter with it. The filter characteristic of the mechanical filter can thereby be adapted in a simple way to the size of the particle to be examined or treated. Optionally, the substrate board can also be constructed as a bendable foil. The chip arrangement is then even better handleable.

The chip arrangement can be manufactured in an even more cost-effective way, if the substrate board has at least four board parts arranged in a plane, if board parts adjacent to one another are connected to each other respectively on their edge areas that face each other, preferably by an adhesive, and if the opening is formed by an open space located between the board parts. An expensive drilling of the opening, for example using ultrasound or a laser beam, can thereby be avoided. Also, a burr on the edge of the substrate board bordering the opening, as can occur for example during laser drilling, can be prevented. The individual board parts preferably each have straight edges and can, for example, be cut to size by grinding or sawing.

It is especially advantageous if at least two first board parts each have at least one straight edge area, with which they can be arranged parallel to each other and facing each other, and if at least two second board parts are arranged between the first board parts in the extension direction of the straight edge areas, spaced apart from each other by the opening, where these two second board parts are respectively connected at their edges that run parallel to each other by the straight edge areas of the first board parts, especially by an adhesive. The first and second board parts lying on each other can then be moved against each other, prior to the application of the adhesive, in the direction of their straight edge areas, whereby the lengths of the opening located in the substrate board are changed in a simple manner and can be adapted to the dimensions of the carrier chips to be inserted in it.

Expediently, the front side end area of the carrier chip arranged transverse to the carrier chip extension plane is covered by an insulation layer, at least in the area of the overhang having the structural component. In this way, in a semiconductor carrier chip, a short-circuit between the substrate of the carrier chip and an electronic structural component, for example a sensor, integrated into the carrier chip is prevented, if the overhang of the carrier chip having the electronic structural component is brought into contact with an electricalally conducting medium, for example a nutrient medium for biological cells.

On the rear side of the substrate board that faces towards the connection contacts, a circuit board can be arranged, which has connection points that are connected or can be connected to the connection contacts. An especially compact design thereby results. The circuit board can have, for example, an evaluation device and/or a control device and/or a power supply for the chip arrangement. This is protected on the rear side of the substrate board prior to contact with a medium to be examined.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

A chip arrangement indicated on the whole by 1 has a substrate board 2 with an opening 3, into which a carrier chip 4 is inserted. The substrate board 2 can, for example, be made of glass or a semiconductor material. The carrier chip 4 has a several electronic structural components 5, constructed as sensors, which are integrated into the carrier chip 4 on the a flat side surface 6 of the carrier chip 4 using methods of semiconductor technology. The individual structural components 5 are each connected to a conductor path 7 with a connection contact 8, on the surface 6 of the carrier chip 4 or running essentially parallel to it, onto which an evaluation and control device can be connected. As can be recognized especially well in FIG. 1, the carrier chip is inserted into the opening 3 of the substrate board 2 in such a way that it extends with its ends beyond the flat side surfaces 9, 9' of the substrate board 2, which face away from each other, and thereby forms the overhangs 10, 10', which project beyond the flat side surfaces 9, 9' of the substrate board 2. Here, the structural components 5 are arranged on the one projection 10 and the electrical connection contacts 8 allocated respectively to them are arranged on the other overhang 10'.

Figure 1:
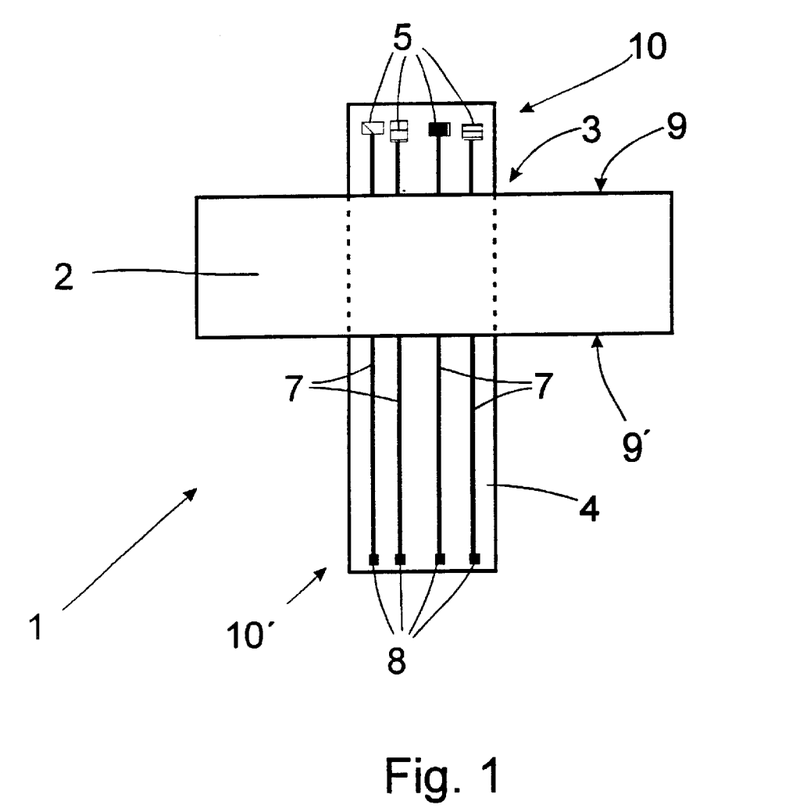
FIG. 1 is a side view of the substrate board with the carrier chip inserted into the opening.
Figure 2:
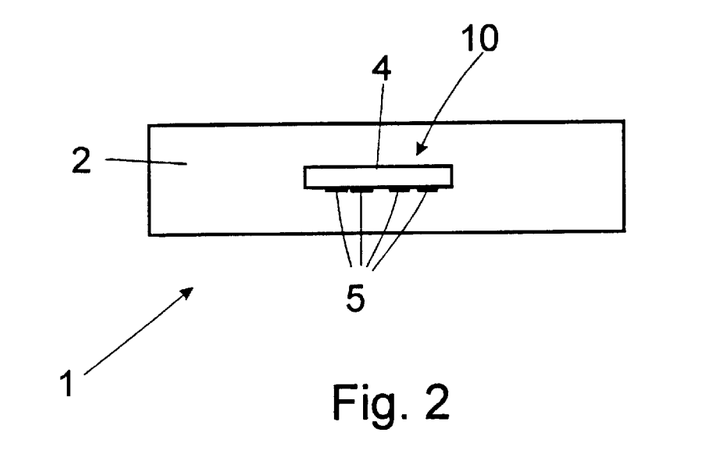
FIG. 2 is a plan view of the chip arrangement according to FIG. 1.

From FIG. 1 it can be clearly recognized that the conductor paths 7 connecting the structural components 5 to the connection contacts 8 pass through the opening 3 of the substrate board 2. The carrier chip 4 is adhered to the edge of the substrate board 2 bordering the opening 3 of the substrate board 2, whereby the adhesive located between this edge and the carrier chip 4 seals off the carrier chip 4 from the substrate board 2. Consequently, the connection contacts 8 located on the rear side of the substrate board 2 are well protected from a medium to be examined, which for example can be a nutrient medium 11 (FIG. 5) having biological cells located therein, and which is located on the front side of the substrate board facing toward the structural components 5, which are constructed as sensors. Corrosion on the connection contacts 8 by components contained in the nutrient medium 11, for example salts or ions, is thus reliably avoided. Since the conductor paths 7 pass through the opening 3 of the substrate board 2, no through-bonding into the substrate board 2 needs to be made in the manufacture of the chip arrangement in order to connect the structural components 5 to the electrical connection contacts 8. The chip arrangement 1 is thus manufactured in a simple and cost-effective manner.

In the embodiment according to FIG. 1, the carrier chip 4 is constructed as a rectangular board, which is arranged with its chip plane and its narrow side surfaces running transverse thereto at respective right angles to the flat side surfaces 9, 9' of the substrate board 2. The surfaces of the substrate board 2 bordering the opening 3 are arranged respectively perpendicular to its flat side surfaces 9, 9'. The opening 3 can thereby be inserted into the substrate board 2 more easily during the manufacture of the chip arrangement.

Figure 4:
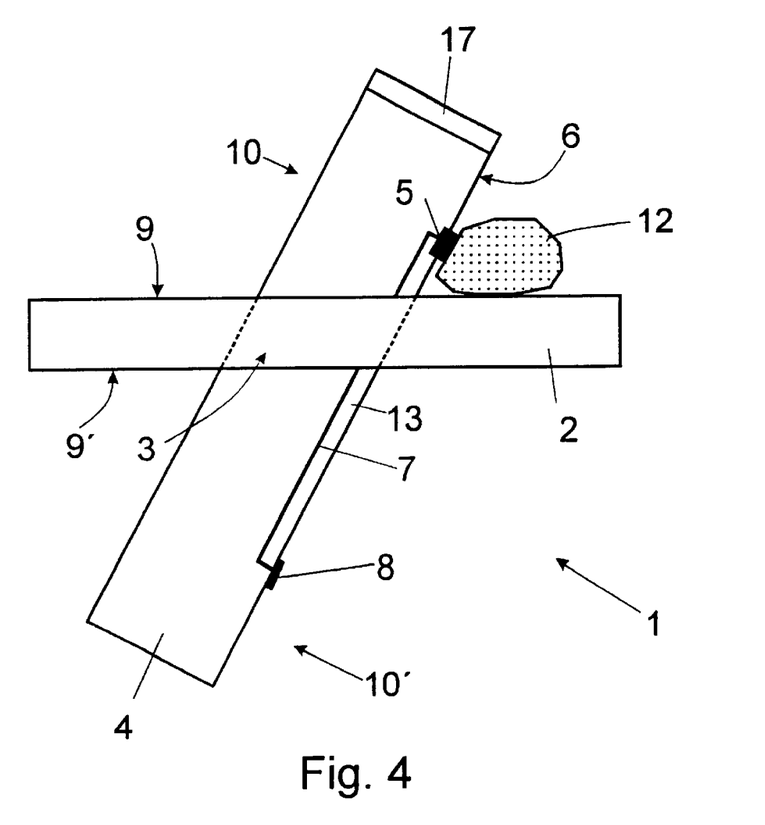
FIG. 4 is a side view of a chip arrangement, in which the extension planes of the substrate board and the carrier chip are tilted towards each other.
Figure 5:
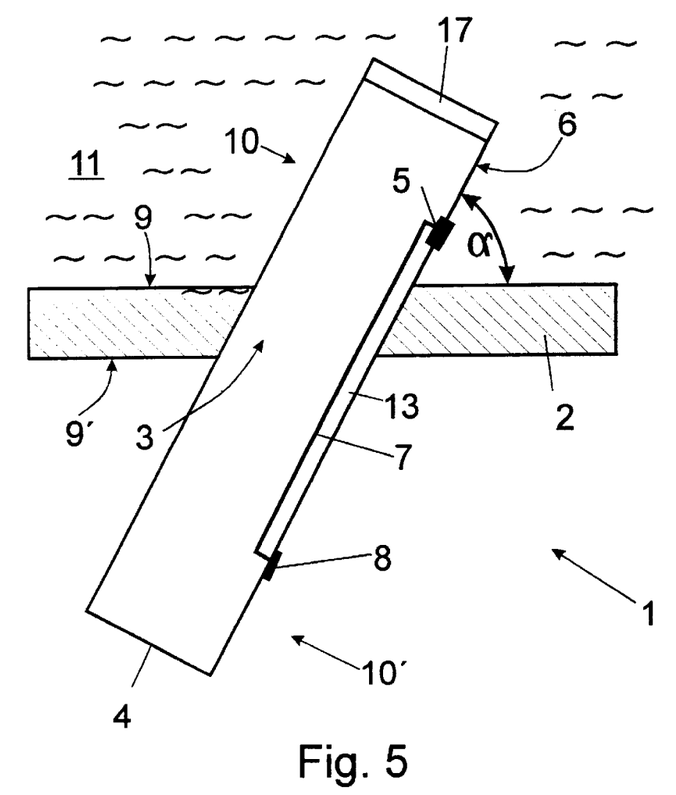
FIG. 5 is a cross section through the chip arrangement shown in FIG. 4.
Figure 6:
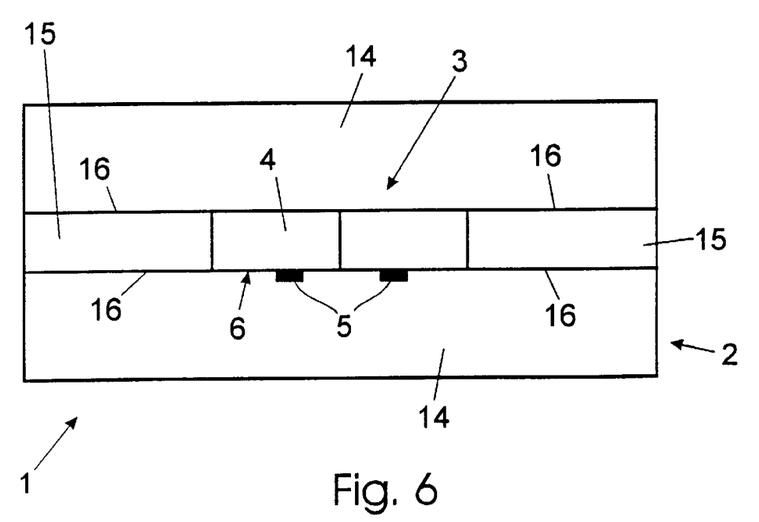
FIG. 6 is a view of the chip arrangement according to FIG. 3, with a substrate board, which has several board parts arranged in a plane and adhered to each other.

In the embodiment according to FIGS. 4 and 5, the carrier chip surface 6 having the structural component 5 and the connection contact 8 is arranged in a plane running at a right angle to the flat side surfaces 9, 9' of the substrate board 2, at a slant angle to these surfaces 9, 9' and encloses an acute angle α with them. The structural component 5 is arranged on the flat side surface 6 of the carrier chip 4 spaced from the edges of this surface 6. The access area to the structural component 5 is thus limited by the carrier chip 4 and the substrate board 2, where the opening angle α of the access area is selected in such a manner that particles which exceed a certain predetermined size can be kept away from the structural component 5.

The chip arrangement 1 shown in FIG. 4 can, for example, be used for the purpose of stripping, with the carrier chip 4, a drop of sweat 12 on the skin surface of a person to be examined. The structural component 5 can be, for example, a glucose sensor. The chip arrangement 1 then makes possible in a simple way, a non-invasive measurement of the glucose content, which is especially advantageous for diabetics, who must determine their glucose content several times a day. The structural component 5 can, however, also be a lactate sensor which can be used, for example, to measure the lactate concentration in the drop of sweat of an athlete. The condition of an athlete can thereby be examined in a simple way.

The structural component 5 can also be an oxygen sensor based on a Clark cell, a nitrogen sensor, a sensor for measuring an ion concentration, or a thermal element. A structural component 5 can, however, also be used which emits an electrical or electromagnetic field, with which a cell located on the substrate board 2 can be influenced or stimulated.

The conductor paths 7 are covered with an electricalally insulating thin film passivation layer 13, which can be made of silicon dioxide, for example. By the passivation layer 13, the conductor paths 7 are well insulated electricalally from the nutrient medium 11. In addition, by the passivation layer 13, corrosion on the conductor paths 7 is prevented by the salts or ions contained in the nutrient medium 11.

Figure 3:
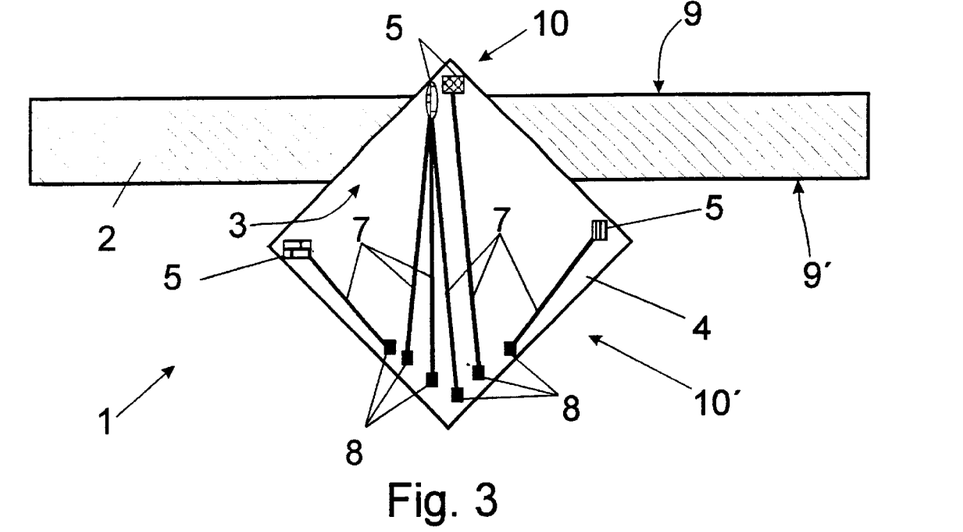
FIG. 3 is a cross-section through a substrate board, into which a carrier chip is inserted, which has a pointed overhang that projects on a flat side of the substrate board and has an electronic structural component.

In the embodiment according to FIG. 3, the cross-section of the overhang 10 having the structural component 5 tapers starting from the flat side surface 9 of the substrate board facing toward the structural component 5 to a pointed edge located on the furthest projecting position of the carrier chip 4. This is formed by a corner area of the carrier chip 4 projecting on the surface 9 of the substrate board 2. As can be recognized especially well in FIG. 3, the carrier chip 4, constructed as an approximately square board, has at this corner area two electronic structural components 5 integrated into the carrier chip 4, which are connected via conductor paths 7 to connection contacts 8, which are arranged on the overhang 10' of the carrier chip 4, located on the opposite, flat-sided surface 9 of the substrate board 2, which faces away from these structural components 5. The pointed overhang 10 of the carrier chip 4, having the structural component 5 constructed as a sensor, can be inserted into a soft body to be examined, for example, a skin layer, where the flat-sided surface 9 of the substrate board 2 functions as a detent surface for the body, which limits the depth that the pointed overhang 10 can be introduced into the body. It is thereby possible to position the structural component 5 in the body or medium to be examined in a simple way at a defined depth, prescribed by the overhang dimension of the overhang 10.

As can be seen from FIG. 3, the carrier chip 4 can be inserted during the assembly of the substrate board 2 in three different rotational positions, relative to the surface normals on the carrier chip plane, into the opening 3 of the substrate board 2, which is approximately trapezoid-shaped in cross-section, where in the individual rotational positions, respective overhangs having different structural components 5 are arranged on the surface 9 of the substrate board 2 which faces towards the measurement object in the use position. These structural components 5 are each connected using the conductor paths 7 that pass through the opening 3 to connection contacts 8, which are arranged on the opposing overhang 10' located on the flat-sided surface 9', that faces away from the measurement object to be examined. In this way, depending on the selection of the position of the carrier chip 4, different chip arrangements 1 can be manufactured. In the embodiment according to FIG. 3, the carrier chip is constructed as a square board. The structural components 5 and the connection contacts 8 are respectively arranged in a corner area of the carrier chip 4. In the chip plane, the carrier chip is arranged, with its edges that pass through the substrate board 2, at a slant angle to the flat-sided surface planes 9, 9' of the substrate board 2. In FIG. 3 it can be clearly recognized that these edges of the carrier chip 4 are respectively inclined at an angle of approximately 45° to the surface planes 9, 9'.

Figure 7:
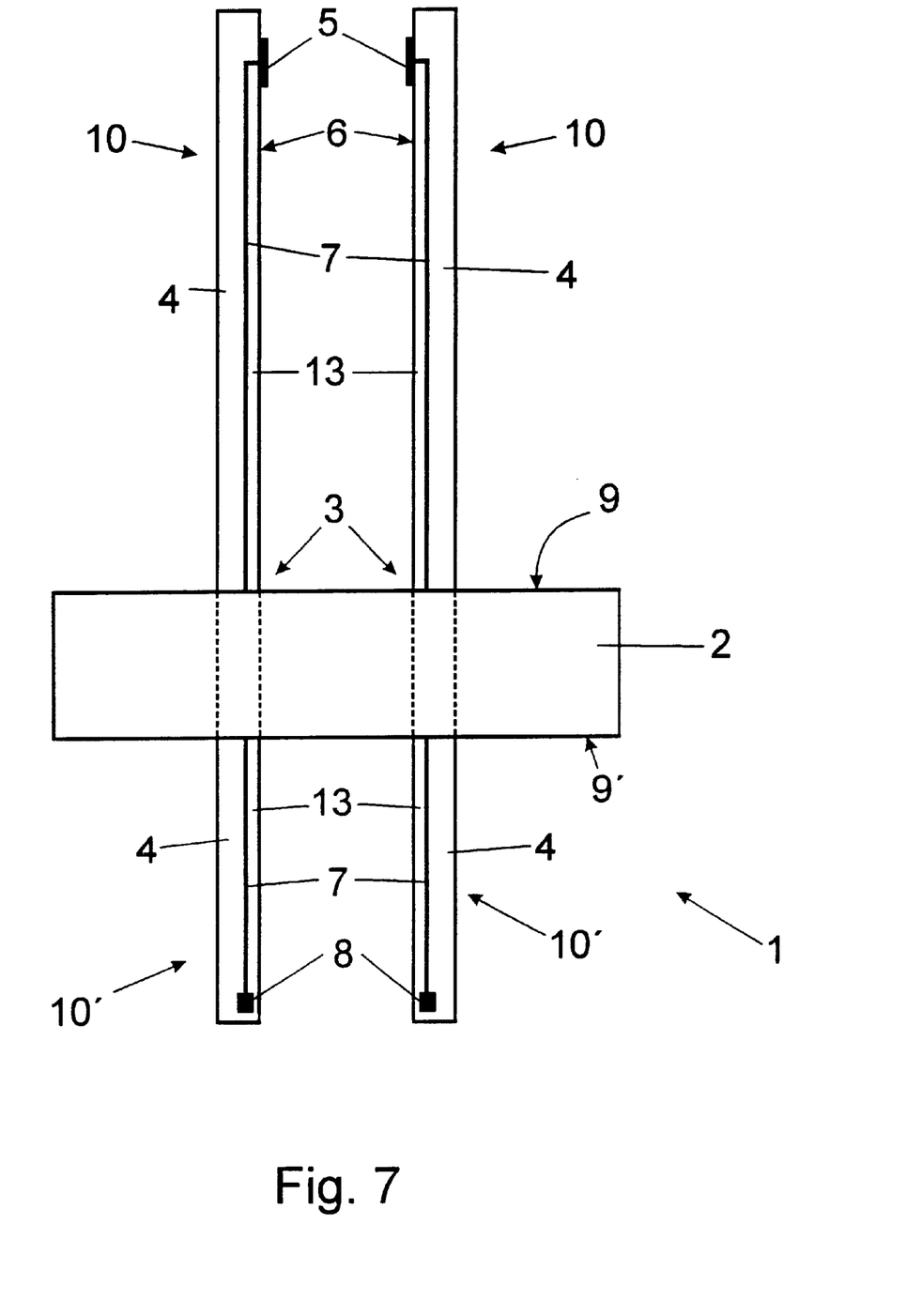
FIG. 7 shows a chip arrangement in whose substrate board two carrier chips are arranged, one of which has an optical emitter and the other has a receiver allocated to this.

FIG. 7 shows a chip arrangement having a substrate board 2 that has openings 3 for two carrier chips 4, 4' allocated to each other, where one of the carrier chips 4 has an optical emitter as a structural component 5 and the other carrier chip 4 has an optical receiver. Between the optical emitter and receiver, a measurement stretch is formed. The chip arrangement can be used, for example, for transmitted light or scattered light measurement and/or as a light barrier.

In the embodiment according to FIG. 7, the substrate board 2 has four board parts arranged in a plane, namely two first board parts 14 and two second board parts 15. The first board parts 14 each have a straight edge area 16, with which they are arranged facing each other and parallel to each other. The second board parts 15 are arranged next to each other in the extension direction of the straight edge areas 16, spaced from each other by the opening 3 between the first board parts 14. On their longitudinal edges running parallel to each other, they are each adhered to a straight edge area 16 of a first board part 14. It is thereby possible in the manufacture of the chip arrangement 1 to move the carrier chip 4 along a straight line running perpendicular to the extension plane of the substrate board 2, in order to adjust the overhang dimension or the tip height of the overhang 10 having the structural component 5. For this purpose, at least one of the second board parts 15 is moved in the board plane parallel to the straight edge areas 16 of the first board parts 14, in order to adapt the dimensions of the opening 3 to the respective position of the carrier chip 4. On the whole, a structural unit results, consisting of the board parts 14, 15 and the carrier chip 4, with which chip arrangements 1, having overhangs 10 that project at variable distances beyond the surface 9 of the substrate board 2, can be manufactured in a simple way.

In the embodiment according to FIG. 4, the front end area of the carrier chip 4, arranged transverse to the carrier chip extension plane, is covered by an insulation layer 17 in the area of overhang 10 having the structural component 5. A current flow from the electrical structural component 5 via the electrically conducting nutrient medium 11 into the substrate of the substrate board 2 is thereby prevented.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A chip arrangement (1) comprising a substrate board (2) having at least one opening (3) and flat-sided surfaces (9, 9') facing away from each other, a carrier chip (4) inserted into the opening, a surface of the carrier chip having at least one integrated conductor path (7) connecting at least one electrical or electronic structural component (5) with at least one electrical connection contact (8), wherein the carrier chip (4) is inserted into the opening (3) in such a manner that its ends project beyond the flat-sided surfaces (9, 9') and thereby form overhangs (10, 10'), at least one of the structural component(s) (5) being arranged on one of the overhangs (10) extending beyond one of the flat-sided surfaces (9), and at least one of the connection contact(s) (8) being arranged on the other overhang (10') extending beyond the other flat-sided surface (9'), the conductor path (7) connecting the structural component (5) and the connection contact (8) to each other passing through the opening (3) of the substrate board (2), and a seal provided between the substrate board (2) and the carrier chip (4), and wherein the carrier chip surface having the electrical or electronic structural component (5) is arranged at an incline to the flat-sided surfaces (9, 9') of the substrate board (2) and encloses an acute angle with it.

2. The chip arrangement according to claim 1, wherein the carrier chip (4) is detachably connected to the substrate board (2).

3. The chip arrangement according to claim 1, wherein the carrier chip (4) is adhered to a wall area of the substrate board (2) which borders the opening (3).

4. The chip arrangement according to claim 1, wherein the carrier chip (4) is arranged with its extension plane at a right angle to a flat-sided surface (9, 9') of the substrate board (2).

5. The chip arrangement according to claim 1, wherein the conductor path(s) (7) is (are) covered with an electrically insulating thin film passivation layer at least in an area of the overhang (10) having the electrical or electronic structural component (5).

6. The chip arrangement according to claim 1, wherein a cross-section of the overhang (10) having the electrical or electronic structural component (5) tapers as it proceeds out from the surface (9) of the substrate board (2) to a position of the overhang (10) that projects furthest outward.

7. The chip arrangement according to claim 1, wherein the carrier chip (4) is insertable in at least two different positions into the opening (3) of the substrate board (2) during assembly of the chip arrangement (1), in one of these positions at least one electrical or electronic structural component (5) is arranged on an overhang (10) of the carrier chip (4) extending beyond a flat-sided surface (9) and the connection contact(s) (8) allocated to this(these) structural component(s) (5) is arranged on the overhang (10') extending beyond another flat-sided surface (9'), and in another position of the carrier chip (4) the structural component(s) (5) and the connection contact(s) (8) are arranged on the same overhang (10, 10') of the carrier chip (4) extending beyond one of the flat-sided surfaces of the substrate board (9, 9').

8. The chip arrangement according to claim 1, wherein an ion-impermeable membrane is arranged on the electrical or electronic structural component (5).

9. The chip arrangement according to claim 1, wherein the substrate board (2) has in a measurement or active space area of the electrical or electronic structural component (5) at least one projection, which forms a mechanical filter together with one of the overhangs (10) having the structural component.

10. The chip arrangement according to claim 9, wherein the electrical or electronic structural component (5) is connected to an evaluation and/or control unit integrated into the carrier chip (4).

11. The chip arrangement according to claim 9, wherein the projection is formed by overhang of a small board inserted into the opening (3) of the substrate board (2).

12. The chip arrangement according to claim 1, wherein a body rests on the carrier chip (4) and covers the electrical or electronic structural component (5), and wherein as a spaceholder is arranged on the carrier chip (4) at least one area projecting laterally beyond a surface plane of the structural component (5) and lying against the body and/or on the body an area projecting laterally over the surface area covering the structural component (5) and lying against the carrier chip (4), such that between the structural component (5) and the body an open space or gap forms an access to the structural component.

13. The chip arrangement according to claim 1, wherein the carrier chip surface having the electrical or electronic structural component (5) and a facing surface of the projection arranged in an area of measurement or active space of the structural component (5) run at a slant to each other in a funnel shape in a surface plane of the substrate board (2).

14. The chip arrangement according to claim 13, wherein a spacing between the electrical or electronic structural component (5) and the projection(s) arranged in the area of its (their) measurement space or active space is adapted to a diameter of a biological cell in a range of greater than 4 $\mu$m to less than 55 $\mu$m.

15. The chip arrangement according to claim 1, wherein at least two carrier chips (4) are inserted into the substrate board (2), one of the carrier chips (4) having at least one structural component (5) constructed as a radiation emitter and another carrier chip (4) having at least one structural component (5) constructed as a receiver and allocated to the radiation emitter, and wherein a measurement section is arranged between the radiation emitter and the receiver.

16. The chip arrangement according to claim 1, wherein the substrate board (2) comprises an elastic material.

17. The chip arrangement according to claim 1, wherein the substrate board (2) has at least four board parts (14, 15)

arranged in a plane, board parts (14, 15) adjacent to one another being connected to each other respectively on their facing edge areas that face each other, and the opening (3) being formed by an open space located between board parts (14, 15).

18. The chip arrangement according to claim 17, wherein the adjacent board parts (14, 15) are connected by an adhesive.

19. The chip arrangement according to claim 1, wherein at least two first board parts (14) each have at least one straight edge area (16) respectively arranged parallel to and facing each other, wherein between the first board parts (14) in an extension direction of the straight edge areas (16) at least two second board parts (15) are arranged spaced from each other by the opening (3), and wherein the two second board parts are each connected at their edges running parallel to each other by the straight edge areas (16) of the first board parts (14).

20. The chip arrangement according to claim 1, wherein a front side end area of the carrier chip arranged transverse to an extension plane of the carrier chip is covered by an insulation layer (17) at least in an area of the overhang having the structural component.

21. The chip arrangement according to claim 1, wherein on a rear side of the substrate board facing the connection contacts (8) a circuit board is arranged, the circuit board having connection points connected or connectable to the connection contacts (8).

22. The chip arrangement according to claim 1, wherein the electrical or electronic structural component (5) comprises a sensor.

23. A chip arrangement (1) comprising a substrate board (2) having at least one opening (3) and flat-sided surfaces (9, 9') facing away from each other, a carrier chip (4) inserted into the opening, a surface of the carrier chip having at least one integrated conductor path (7) connecting at least one electrical or electronic structural component (5) with at least one electrical connection contact (8), wherein the carrier chip (4) is inserted into the opening (3) in such a manner that its ends project beyond the flat-sided surfaces (9, 9') and thereby form overhangs (10, 10'), at least one of the structural component(s) (5) being arranged on one of the overhangs (10) extending beyond one of the flat-sided surfaces (9), and at least one of the connection contact(s) (8) being arranged on the other overhang (10') extending beyond the other flat-sided surface (9'), the conductor path (7) connecting the structural component (5) and the connection contact (8) to each other passing through the opening (3) of the substrate board (2), and a seal provided between the substrate board (2) and the carrier chip (4), and wherein the carrier chip (4) is insertable during assembly of the chip arrangement (1) into at least two different positions in the opening (3) of the substrate board (2), the carrier chip (4) having at least two electrical or electronic structural components (5), which are respectively connected by at least one conductor path (7) with at least one electrical connection contact (8) respectively allocated to them, and depending on a selected position of the carrier chip (4), at least one of these structural components (5) is arranged respectively on one of the overhangs (10) of the carrier chip (4) extending beyond a flat-sided surface (9) of the substrate board (2) and the connection contact(s) (8) allocated to this (these) structural component(s) (5) are arranged on another of the overhangs (10') extending beyond the other flat-sided surface (9').

\* \* \* \* \*